(12) United States Patent
Richerdt et al.

(10) Patent No.: US 10,338,041 B2
(45) Date of Patent: Jul. 2, 2019

(54) DERIVATIZATION APPARATUS AND METHOD

(71) Applicant: CAMAG, Muttenz (CH)

(72) Inventors: Nicolas Richerdt, Michelbach le bas (FR); Eike Reich, Rheinfelden (CH); Mark Howell Sturgess, Basel (CH); Diego Micha Haldemann, Liestal (CH)

(*) Notice: Subject to any disclaimer, the term of this patent is extended or adjusted under 35 U.S.C. 154(b) by 225 days.

(21) Appl. No.: 15/486,656

(22) Filed: Apr. 13, 2017

(65) Prior Publication Data

US 2017/0299560 A1    Oct. 19, 2017

(30) Foreign Application Priority Data

Apr. 19, 2016 (CH) .................................. 00518/16

(51) Int. Cl.
| | | |
|---|---|---|
| *G01N 30/94* | (2006.01) | |
| *B05B 1/00* | (2006.01) | |
| *B05B 13/04* | (2006.01) | |
| *B05B 17/00* | (2006.01) | |
| *B05D 1/00* | (2006.01) | |
| *B05B 7/00* | (2006.01) | |
| *B05B 5/00* | (2006.01) | |
| *B05D 1/04* | (2006.01) | |
| *C23C 16/455* | (2006.01) | |
| *C23C 16/448* | (2006.01) | |
| *B05B 17/06* | (2006.01) | |
| *B05B 16/60* | (2018.01) | |

(52) U.S. Cl.
CPC .............. *G01N 30/94* (2013.01); *B05B 13/04* (2013.01); *B05B 13/0405* (2013.01); *B05B 17/0638* (2013.01); *B05D 1/60* (2013.01); *B05B 5/00* (2013.01); *B05B 7/0012* (2013.01); *B05B 16/60* (2018.02); *B05B 17/0615* (2013.01); *B05D 1/04* (2013.01); *C23C 16/4486* (2013.01); *C23C 16/45563* (2013.01); *G01N 2030/945* (2013.01)

(58) Field of Classification Search
CPC . B05B 13/0405; B05B 16/60; B05B 17/0638; B05B 13/04; B05B 17/0615; B05B 5/00; B05B 7/0012; B05D 1/60; B05D 1/04; G01N 2030/945; G01N 30/94; C23C 16/4486; C23C 16/45563
See application file for complete search history.

(56) References Cited

U.S. PATENT DOCUMENTS

| | | | | |
|---|---|---|---|---|
| 3,840,391 | A * | 10/1974 | Spitz | .................. B05B 17/0615 239/102.2 |
| 5,451,260 | A * | 9/1995 | Versteeg | ............. C23C 16/4486 118/725 |
| 5,823,428 | A | 10/1998 | Humberstone et al. | |
| 6,045,864 | A * | 4/2000 | Lyons | ...................... B05D 1/60 427/255.23 |
| 6,127,082 | A * | 10/2000 | Humberstone | ......... B05B 5/025 118/621 |
| 6,235,112 | B1 * | 5/2001 | Satoh | .................. C23C 16/4408 117/102 |

(Continued)

*Primary Examiner* — Jennifer Wecker
(74) *Attorney, Agent, or Firm* — Donald J. Ersler

(57) ABSTRACT

A derivatization apparatus and method for coating a sample carrier with a reagent solution. The derivatization apparatus consists of a closed system in which a small quantity of reagent solution is sprayed into a closed container via a spray nozzle. A sample carrier is located in the closed container and is coated as homogeneously as possible with the reagent solution.

19 Claims, 6 Drawing Sheets

(56) References Cited

U.S. PATENT DOCUMENTS 6,349,668 B1 * 2/2002 Sun .......................... B05B 5/00
   118/723 E
2016/0228902 A1 * 8/2016 Crichton ............... A61M 35/00

* cited by examiner

DERIVATIZATION APPARATUS AND METHOD

CROSS REFERENCE TO RELATED APPLICATION

This is a patent application claiming priority from patent application no. 00518/16, filed in Switzerland on Apr. 19, 2016.

BACKGROUND OF THE INVENTION

The present invention relates to a derivatization apparatus for coating a sample carrier with a reagent solution and to a derivatization method for coating a sample carrier with a reagent solution.

In the field of thin-layer chromatography, the derivatization of samples to be analyzed is frequently carried out by immersing the sample carrier in a solution with reagents or coating the sample carrier with the solution which then penetrates the sample carrier and/or the sample depending on the desired application.

The spraying is known to have the great advantage over the immersion that the measuring areas are less blurry or not blurry at all. A further advantage is the reduced need for reagents required as solvents.

In order to achieve the best results or for the subsequent chemical reaction to run successfully, it is desirable that the reagent solution be applied as homogeneously as possible on the entire sample carrier in an optimum dosage and thickness. If a spraying method is used, this depends on the type of spray head used and on the distance and the exact position of the spray head with respect to the sample carrier. In order to achieve a more uniform distribution, the spray head may also be moved above the sample carrier in such a way that all areas are sprayed evenly.

A typical spray method produces small liquid droplets which are sprayed onto the sample carrier. A certain area may be sprayed more or less evenly depending on the shape of the spray head. This produces a liquid film on the surface of the sample carrier which triggers the desired reaction.

In addition to the direct spraying of the sample carrier, it is also possible to form a mist of fine droplets by means of a spray nozzle, which then settles onto the sample carrier. WO 2006/114249 discloses such a method and a corresponding apparatus, whereby the homogeneous distribution as well as the need for reagents are optimized by nebulizing the reagent solution. The liquid droplets are produced by ultrasonic atomization. This creates a mist above the liquid in the container, which then settles and deposits the desired liquid film on the sample carrier.

The size of the droplets generated by an ultrasonic atomizer depends on the vibration frequency. The size of the generated drops may vary by up to 25% depending on the frequency selected. This leads to a relatively inhomogeneous mist, and thus to an inhomogeneous liquid film on the sample carrier.

To somewhat obviate this problem, a droplet separator is used in the above-described method in order to prevent too large drops or splashes generated by the spray nozzle from reaching the sample carrier. However, in order to achieve a complete covering of the sample carrier with a liquid film of the reagent solution, an excess of reagent liquid is necessarily present either in the lower part of the liquid container or caught onto the droplet separator before the liquid drops back down into the liquid container next to the sample carrier.

The referenced patent document also shows a gas inlet and/or outlet used to swirl the generated mist in the container in order to achieve a better intermixing and eliminate inhomogeneities in the distribution of the mist.

SUMMARY OF THE INVENTION

The present invention provides improvements to the known derivatization apparatuses and methods in such a manner that the advantages of the known derivatization apparatuses and methods are maintained. In particular, a first object of the present invention is to generate an homgeneous mist of droplets whose sizes vary in a narrow range around the target value. A second object of the present invention is to allow the sample carrier to be sprayed evenly. A third object of the present invention is to make the necessary excess of reagent solution as small as possible and provide an apparatus suitable for operation with toxic and/or highly reactive substances.

DETAILED DESCRIPTION

The apparatus of the present invention is a derivatization apparatus for coating a sample carrier 2 with a reagent solution. The embodiment shown in FIG. 1 consists of a closed system in which a small amount of reagent solution is sprayed into a hermetically sealed container 1 via a spray nozzle 3. A sample carrier 2 is located in the sealed container 1 and is to be coated as homogeneously as possible with the reagent solution.

Figure 1:
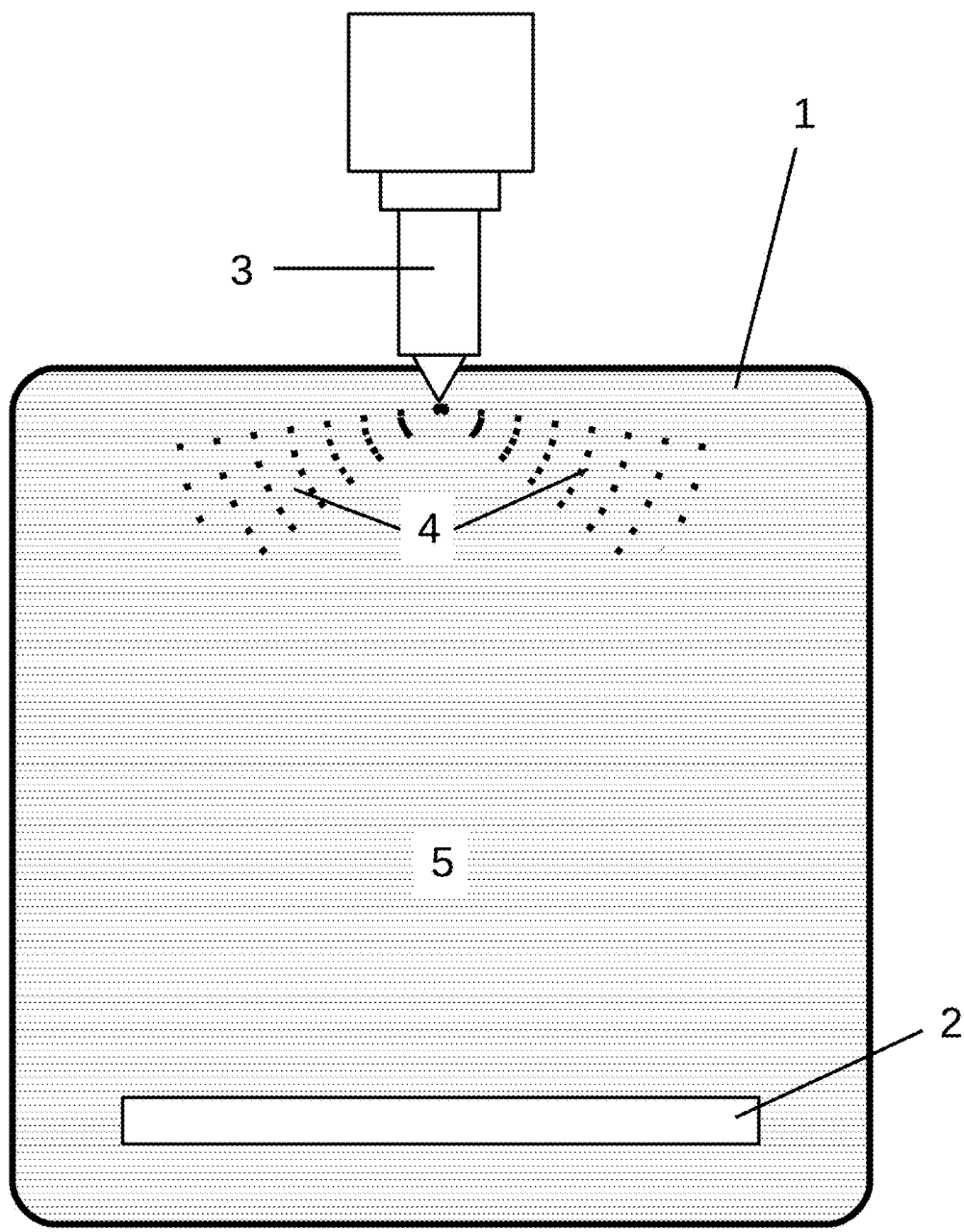
FIG. 1 Derivatization apparatus with the spray nozzle arranged above the sample carrier.
Figure 2:
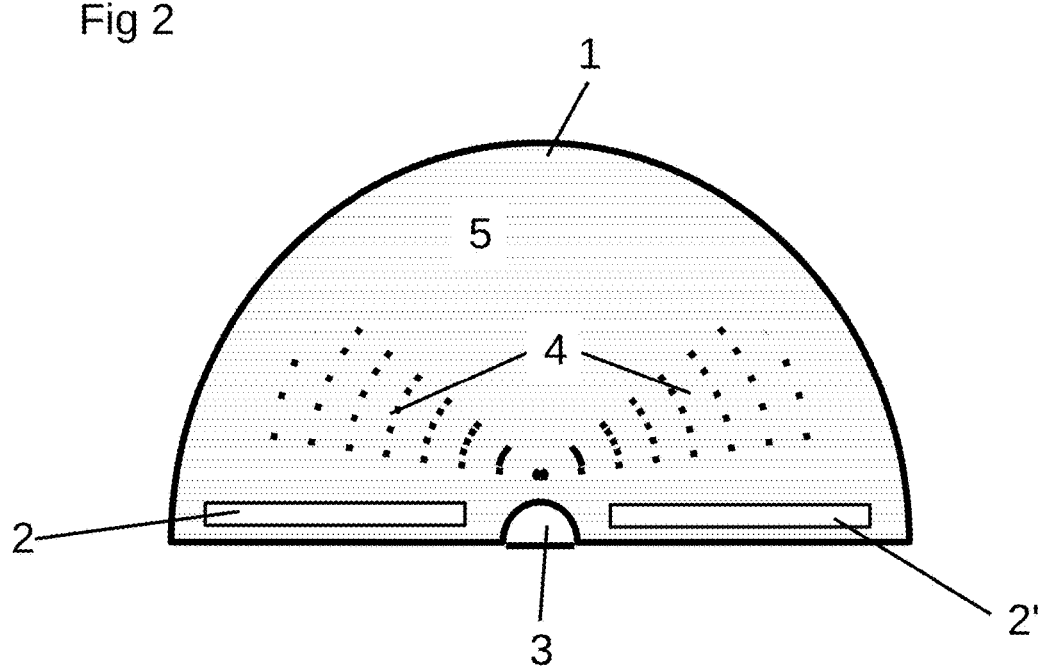
FIG. 2 Derivatization apparatus with the spray nozzle arranged beside the sample carrier.

FIGS. 1 and 2 show possible arrangements of the spray nozzle 3, which may be centred in the middle of the upper or lower wall of the sealed container 1. Further arrangements of the spray nozzle 3 in the direction of the side walls of the container 1 (asymmetrical) or even on the side walls are also possible. The spray nozzle 3 produces a homogeneous mist 5 of droplets 4 of the reagent solution, the droplets 4 having a uniform size. In the embodiments shown in the figures, a mist 5 is produced in the upper region of the container 1. Due to the gravitational force, this mist 5 settles slowly and forms a homogeneous liquid layer of the reagent solution on the sample carrier 2.

Ideally, the container 1 is only minimally wider than the size of the sample carrier 2 in order to ensure that as little as possible of the reagent solution lands beside the sample carrier 2. This has the great advantage that very little excess of reagent solutions is required, which, in the case of expensive or poisonous solutions, may then have to be disposed of or collected again with great effort for further use and to be recycled.

A further embodiment of the derivatization apparatus is shown in FIG. 2. The container 1 has a bell shape or the shape of an hemisphere. Other forms, e.g. a half-ellipsoid, a cylinder or a cube as shown in FIG. 1 are also possible. In this embodiment, the spray nozzle 3 is located in the lower part of the container 1, the droplets 4 being sprayed upwards into the entire volume of the container 1 in order to generate the mist 5. This has the advantage over the embodiment of FIG. 1 that all liquid droplets 4 are first sprayed upwards, where they then briefly come to a standstill in the vertical direction before slowly settling downwards again by gravity in a mist 5 and eventually forming the desired coating on the sample carrier 2. In this embodiment, the sample carrier 2 is located beside the spray nozzle 3, whereby the spray nozzle 3 may also be arranged laterally in the container 1 in case a larger sample carrier 2 is to be accommodated in the container 1. A further embodiment of the derivatization apparatus may also feature two or more sample carriers 2, 2' arranged around the spray nozzle 3 so that all can be sprayed simultaneously with the same reagent solution.

An essential requirement of the present invention is to avoid contamination by the reagents and carryovers which could skew the analyses. Contamination is generally critical, all the more if the reagent solution is a toxic substance, which may destroy the sample or even the sample carrier 2 or other facilities in the environment.

Figure 4:
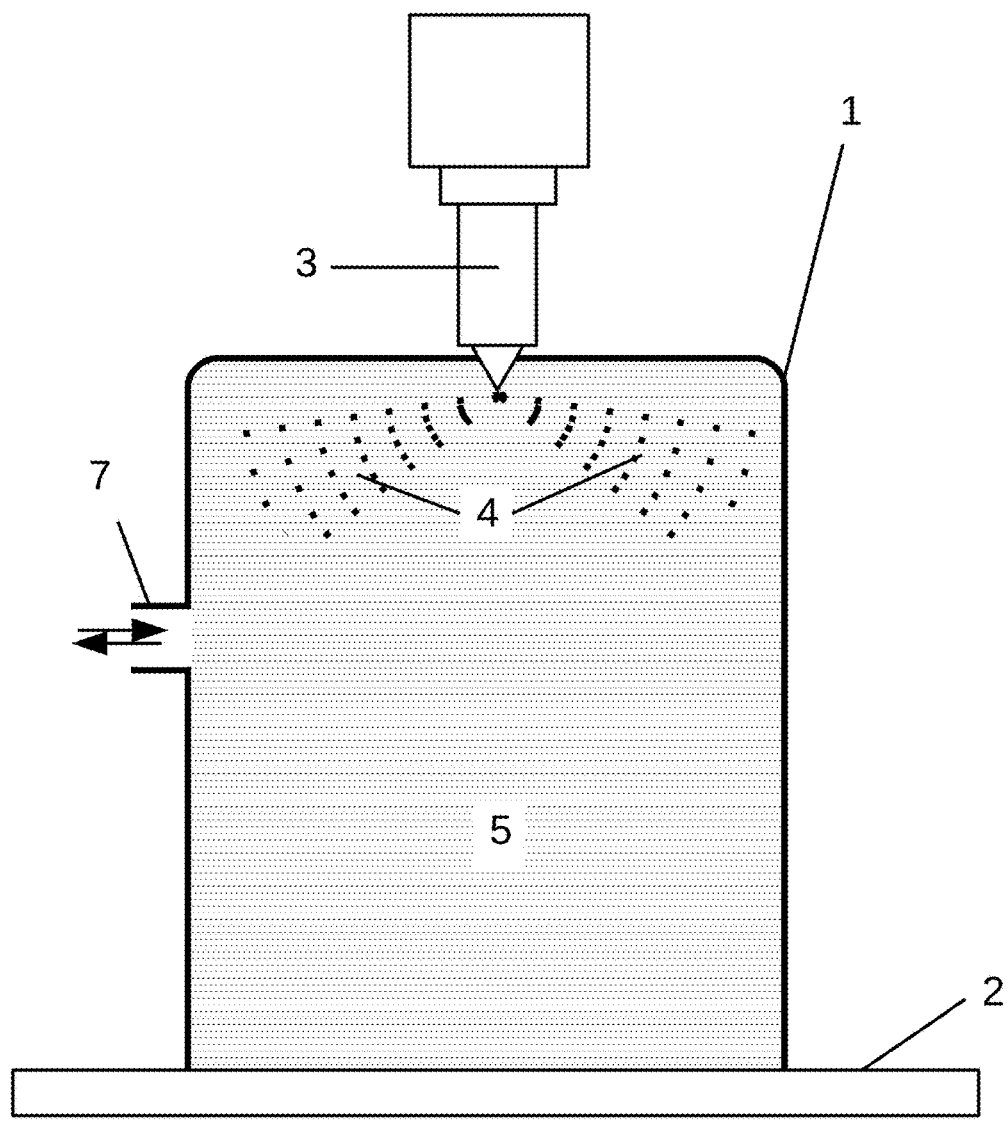
FIG. 4 Derivatization apparatus, with the container in the form of a hood.
Figure 5:
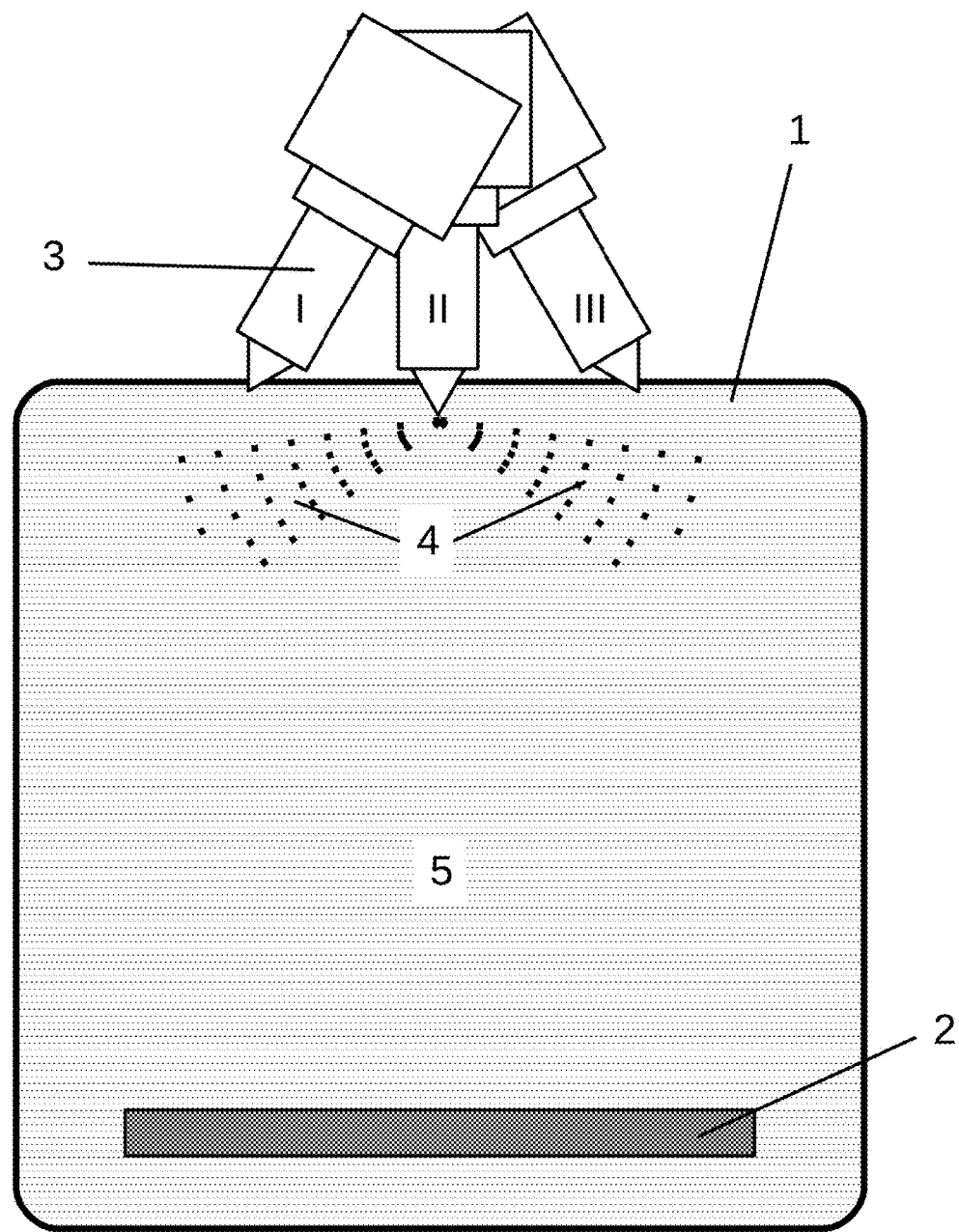
FIG. 5 Derivatization apparatus with a movable spray nozzle
Figure 6:
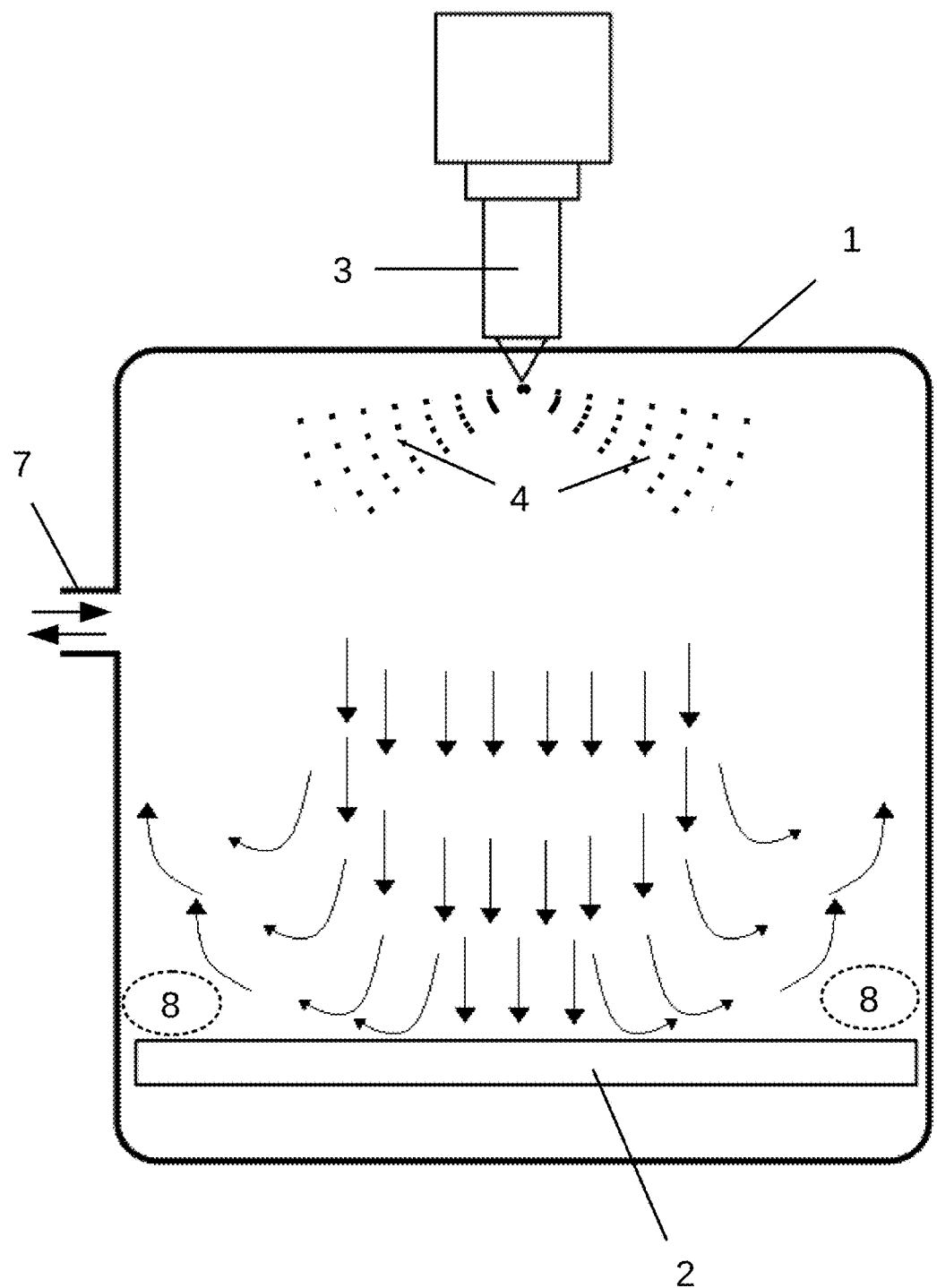
FIG. 6 Streamlines of the mist in the container
Figure 7:
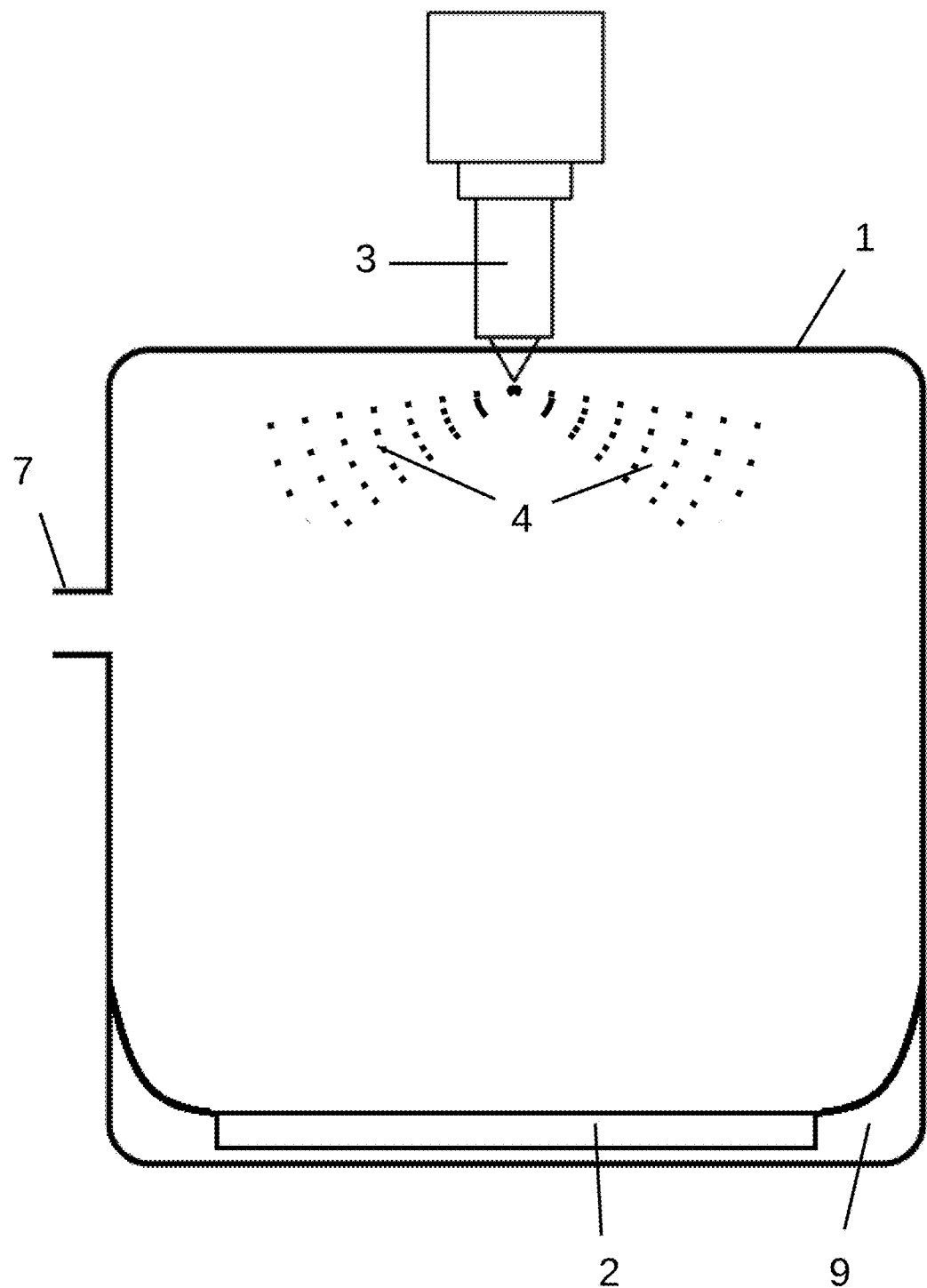
FIG. 7 Derivatization apparatus with curved mounting

Contamination may occur as soon as the container 1 is opened after the coating. If the mist 5 has not yet settled completely, the remnants of the mist 5 may spread and deposit in the environment. In order to avoid this, the mist 5 may be completely extracted out of the container 1 after the coating and before opening it. The container 1 may even be refilled with clean air. This is effected via one or more ventilation openings 7 and a suction device, such as a pump for example (FIG. 4).

Reagents may also deposit onto the inner walls of the container 1. When coating a new sample carrier 2, these reagents may have undesirable effects, especially if a different reagent liquid is used for generating the mist 5. A possible solution for avoiding such deposits is to coat the walls of the container 1 with a material or to treat them in such manner that they are made unsuitable for the deposition of the droplets 4. In addition, the container 1 should be dishwasher-safe and easy to clean so that any deposits can be removed by thorough washing.

Carryovers and contamination also occur when the sample carrier 2 is picked up and moved for further processing. In the embodiment of FIGS. 1 and 2, the sample carrier 2 is completely enclosed in the container 1 and its entire surface is coated with the reagent solution. When seizing the sample carrier 2 for moving it, reagent solution is deposited on the seizing arm or the moving device since these come into contact with the sample carrier 2 coated with reagent liquid. In this embodiment, it is also possible for droplets 4 to be deposited on the other surfaces of the sample carrier 2, in particular on the underside.

Figure 3:
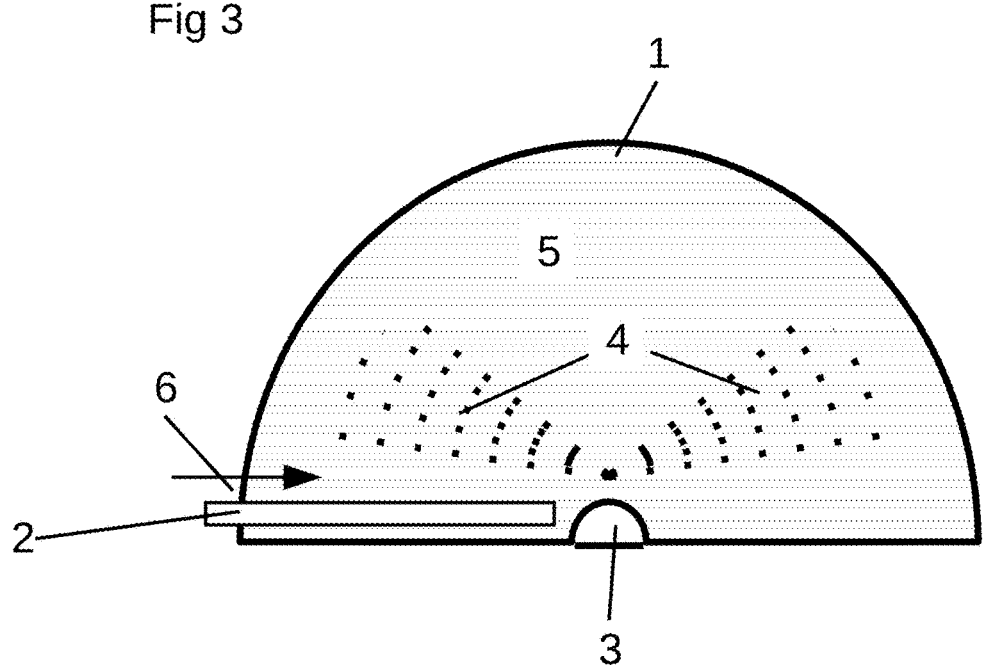
FIG. 3 Derivatization apparatus with an insertable sample carrier.

This becomes problematic when the sample carrier 2 is removed from the derivatization device after the coating has taken place. Any object, be it a gripper or a conveyor belt for instance, coming into contact with the sample carrier 2 is contaminated with the reagent solution and may spread it further. This is particularly undesirable in the case of toxic substances. Possible solutions are shown in the embodiments of FIG. 3 and FIG. 4, whereby only part of the sample carrier 2 is located within the closed container 1 during the coating process. The part of the sample carrier 2 permanently outside the container 1 may be safely seized for transporting the coated sample carrier 2 for further processing.

According to the embodiment of FIG. 3, the part of the sample carrier 2 to be coated is inserted into the container 1 before the coating through an opening 6. In order to make sure that the surface of the sample carrier 2 does not touch the container 1 upon insertion or removal through the opening 6, the opening 6 must be larger than the part of sample carrier 2 which is to be coated. In order to prevent reagent solution from escaping from the container 1, the sample carrier 2 and the container 1 must be designed in the region of the opening 6 in such a way that the container 1 still seals hermetically for the spraying operation. This can be done according to many known methods. For example, it is possible to widen the outer part of the sample carrier 2, so that it is bigger than the opening 6 and completely fills it. A projection bigger than the opening 6 may also be arranged at the outer end of the sample carrier 2, so that the container 1 is sealed after complete insertion of the sample carrier 2 into the opening. In order to achieve a better seal, additional different material may also be arranged on the sample carrier 2 or around the opening, for example seals made of rubber or polymer.

As an alternative to the described method with an opening 6 in the container 1, the container 1 may also consist of a hood 1 lowered onto the sample carrier 2 (FIG. 4). This can be done manually or automatically by means of a machine with a motor. As in the embodiment with an opening 6, the hood 1 and sample carrier 2 must be tightly sealed together before the spraying operation. Thus, only a certain region of the upper side of the sample carrier 2 is isolated in the container 1, onto which the reagents settle. The edges and the underside of the sample carrier 2 can then be handled without the risk of spreading reagents. This may be done with a gripper or a conveyor belt for example.

The embodiments of FIGS. 3 and 4 also allow the integration the presented derivatization apparatus into a semi-automatic or fully automated process in which the sample carrier 2 is transported from one processing station to the next. For example, this may happen manually, by means of a conveyor belt or by means of a robotic arm. The embodiment of FIG. 3 only shows a possible arrangement of the opening 6, which may be arranged at other locations in the container 1.

The tight seal of the container 1 must also be ensured in the area of the spray nozzle 3. In a possible embodiment as shown in FIG. 2, the entire spray nozzle 3 may be arranged in the container 1. In case the reagent solution cannot be introduced from the outside, the reagent solution for the coating must be located in a reservoir arranged inside of the container 1. In FIG. 1, only the spray head is located inside the container 1, the remaining part of the spray nozzle 3, as well as the reservoir with the reagent solution, are located outside the container 1. In this arrangement, it must be ensured that the container 1 is tightly closed around of the spray head.

The following values are crucial for the homogeneous coating of the sample carrier 2 by generation and settling of a mist 5: the droplet size, the deviation of the droplet sizes from the target value and the homogeneous distribution of the droplets 4 in the container 1.

The desired droplet size can vary greatly depending on the application, for example depending on the type of reagent solution (in particular depending on viscosity) or desired homogeneity: the finer the droplets 4 and the mist 5, the slower the coating process and the more homogeneous the coating is after longer spraying times. For the present coating process, the diameter of the droplets 4 is preferably less than 12 µm, and optimally between 4 µm and 12 µm.

Each spray head is preferably interchangeable and consists of a porous material whose pore size is suitable for a particular application. The pore size is preferably uniform. The smaller the pores and the more viscous the reagent solution, the more difficult it is to drive the reagent solution through the spray head and produce droplets 4. The spray heads are thus selected according to the viscosity of the reagent solution and the desired droplet size.

The deviation of the droplet sizes from the target value must be as low as possible, preferably with tolerances of less than 15%, in order to produce a uniform mist 5. This can be achieved by using a "vibrating mesh" spray nozzle 3, for example a piezoelectric nozzle 3. In "vibrating mesh" spray nozzles 3, a membrane featuring several thousands (approx. 1000-7000 for example) laser-cut pores is vibrated in the spray head, which produces a mist 5 of tiny droplets 4 through the pores. Such membranes may be made of a palladium alloy for example. The membrane is vibrated by exciting the spray nozzle 3 with an alternating voltage, for example a sinusoidal voltage, at the resonance frequency. The amplitude of the vibrations is adjusted according to the desired spray quantity and/or speed. The higher the amplitude, the higher the flow of reagent solution through the membrane.

Tests have shown that a homogeneous distribution of the droplets 4 can be achieved more easily when the spray head or the spray nozzle 3 is moved in the container 1. For example, the movement may be oscillating laterally back and forth and/or rotating and/or on a helical path from the outside to the inside or from the inside to the outside. In principle, any kind of movement is possible, but periodic movements ensure a better homogeneity of the coating. A periodic movement, for example at constant speed, allows a uniform spraying of the relevant area of the sample carrier 2. For instance, oscillating movements with an amplitude of +/−30° at a frequency of 1 Hz have shown good results. A possible movement is shown FIG. 5. In this embodiment, the spray nozzle 3 is oscillated back and forth from the position I through the position II to the position III and back again. A planar movement with a deviation of 10-30° from the vertical has proven to be a simple yet efficient method. Instead of a mere planar oscillation, oscillations in several directions are also possible.

The distance between the sample carrier 2 and the spray head proved to play an important role for the homogeneous distribution of the droplets 4. If the sample carrier 2 is too close to the spray head, the droplets 4 can not spread homogeneously over the entire surface of the sample carrier 2 before they settle thereon. This leads to an excess of reagent solution in the vicinity of the spray head on the sample carrier 2, while much less reagent solution settles further away from the spray head. Still, an excessive distance between the sample carrier 2 and the spray head makes the derivatization apparatus unnecessarily large and bulky. Besides, it may be necessary to wait longer for all the droplets 4 to have settled onto the sample carrier 2. In an optimal embodiment, this distance is approximately 20 cm.

The position of the sample carrier 2 within the container 1 is important for the uniformity of the coating. Tests have shown that the droplets 4 of the mist 5 have different speeds in different areas of the container 1. The velocity of the droplets 4 is almost null in the corner region 8 in the vicinity of the inner wall of the container 1 and of the sample carrier 2 (FIG. 6). As a result, fewer droplets 4 are deposited on the sample carrier 2 in this region. In order to achieve a more uniform coating even in the corner region 8, the sample carrier 2 may be arranged on a special curved mounting 9 in the container 1 according a particular embodiment of the present apparatus (FIG. 7). This way, additional droplets 4 are diverted from the corner of the container 1 onto the sample carrier 2 and the quantity of the deposited droplets 4 is more uniform over the sample carrier 2.

The combination of the above-mentioned measures is crucial for depositing a uniform quantity of reagent solution onto the sample carrier 2. By properly selecting the relevant parameters, i.e. the pore size and/or the electrical excitation of the vibrating membrane and/or the type of movement of the spray nozzle 3 and/or the distance between the nozzle 3 and the sample carrier 2, and taking into account the viscosity of the reagent solution, droplets 4 of a precise size, with a low deviation of the droplet size from the target value and with a homogeneous distribution of the droplets 4 within the container 1 can be achieved. Sample carriers 2 with local deviations of the applied amount of reagent solution of less than 10%, advantageously less than 5% and particularly advantageously less than 2% can be achieved with the present apparatus and method.

The derivatization method with the described derivatization apparatus proceeds in several phases. In the first phase, the so-called spraying phase, a small amount of reagent solution is sprayed into the container 1 by means of the spray nozzle 3 in order to produce a mist 5 with droplets 4 of uniform size. The generated droplets 4 then immediately start settling and coating the sample carrier 2. The second phase, the passive settling phase, after spraying is finished, consists in waiting for the remaining droplets 4 to slowly settle onto the sample carrier 2 and to form the desired homogeneous coating with the reagent solution. After a predefined time, a next step may consist in vacuuming the remaining mist 5 out of the container 1 by means of a suction device, so that only the droplets 4 already settled on the sample carrier 2 remain in the container 1. This is particularly helpful for speeding up the process with very small droplets 4 since the settling can take a very long time. A further advantage is that spreading of the reagent solution in the environment is avoided after opening of the container 1. This avoids carryovers, contamination and skewing subsequent analyses.

In order to determine the end of the spraying phase, it is possible to detect a so-called end-of-spray time. This end-of-spray time should be set as accurately as possible to the moment when the reagent fluid is completely exhausted.

This avoids damage to the spray nozzle 3, which can occur if it is operated without liquid. The end-of-spray time can be detected by a change in the current or the voltage of the spray nozzle 3, since the energy demand for vibrating the membrane changes as soon as it runs out of reagent solution. Alternatively, the end-of-spray time may be detected optically, e.g. by means of a light barrier detecting whether solution is still sprayed or not. As soon as this end-of-spray time is reached, the spraying phase is terminated.

The duration of the spraying phase and the passive settling phase depends on the reagent solution used and the amount sprayed. According to an exemplary embodiment of the invention, the spraying phase lasts up to 10 minutes, and the passive settling phase up to one minute. The total duration of the process is therefore less than 11 minutes. However, the duration of the spraying phase and/or the passive settling phase may each be shortened or lengthened independently from one another to achieve special coatings. Depending on the application, the passive settling phase may be very short or even longer than the spraying phase. In particular embodiments, it is also possible to detect the end of the passive settling phase, e.g. visually when no mist 5 is visible in the container 1. Alternatively, the apparatus may be provided with an additional device measuring the light permeability of the contents of the container 1 or any other relevant variable for determining when all the droplets 4 have settled.

In a next possible step of the method, the remaining mist 5 may be removed from the container 1 after a certain time, in particular if the lowering phase is rather long and a number of droplets 4 have not yet settled on the sample carrier 2. This may be done by vacuuming the mist 5 out of the container and can significantly improve the speed of the entire process.

In a further possible embodiment, the sample carrier 2 may be cooled or heated. As a result, certain chemical or physical processes can be optimized, accelerated or even made possible, which would otherwise happen only partially or not at all. The cooling or heating can take place via the bottom of the container 1. The walls of the container 1 could also be brought to a different temperature from outside or via an integrated heating/cooling system. This may further prevent the droplets 4 from depositing onto the walls of the container 1. The heating or cooling of the sample carrier 2 and the walls of the container 1 could also be used to generate a temperature gradient in the container 1 which accelerates or slows the settling of the mist 5.

Depending on the reagent solution used, the spray nozzle 3 may or must be cleaned before the next application. In addition to the cleaning of the container 1, cleaning the spray nozzle 3 is crucial for avoiding carryovers. For example, the spray nozzle 3 may be operated with a neutral liquid or with a special cleaning solution.

The procedure described herein is thus most simple, flexible and efficient. Only a small amount of reagent solution is required to coat the sample carrier 2 completely. The process is suitable for diverse reagents, in particular also for particularly expensive reagent solutions, since only a small amount of material is required. Since the container 1 is tightly sealed during the coating process, highly toxic reagent solutions can also be used without the need for expensive safety measures. Also, shortening the passive settling phase by removing the remaining reagent mist improves the speed of the coating process.

The integration of the presented derivatization method as a single process step into a complete analysis process is straightforward.

The invention claimed is:

1. Derivatization apparatus for coating a sample carrier prior to the analysis of the sample comprising:
   a reservoir for a reagent solution; and
   a spray nozzle with a spray head and a container in which at least a part of the sample carrier is located, wherein said container is hermetically sealed, said spray head is located within said container and is configured to perform a periodic movement of at least from a first position to a second position in said container and relative to a horizontal plane in said container, said reagent solution is configured to be sprayed into said container by said spray head in order to generate in said container a homogeneous mist of droplets of said reagent solution.

2. The derivatization apparatus according to claim 1, wherein
   only part of said sample carrier is located within said closed container.

3. The derivatization device according to claim 1, wherein said container includes a hood which can be lowered onto said sample carrier.

4. The derivatization device according to claim 1, wherein the walls of said container are made or coated with a material which is unsuitable for the deposition of said droplets.

5. The derivatization device according to claim 1, wherein said spray head comprises a membrane of porous material with a uniform pore size.

6. The derivatization device according to claim 5, wherein said membrane is excited and vibrated with an alternating voltage.

7. The derivatization device according to claim 1, wherein said container has at least one ventilation opening which is connected to a suction device.

8. The derivatization device according to claim 1, wherein a homogeneous distribution of said droplets in said container is achieved by a suitable choice of said movement of said spray nozzle and of the distance between said spray head and said sample carrier during the spraying.

9. Method for coating a sample carrier with the derivatization device according to claim 1, wherein in a first spraying phase a spray head effecting a periodical movement in a sealed container produces a homogeneous mist of droplets of a reagent solution in said sealed container in a second passive settling phase said mist slowly settles and coats said sample carrier with a homogeneous liquid film of the reagent solution.

10. The method according to claim 9, wherein
    only a certain region of said sample carrier is coated.

11. The method according to claim 9, wherein
    said spray head is porous and the optimal pore size is selected before each use depending on the viscosity of said reagent solution and the desired drop size.

12. The method according to claim 9, wherein
    said container is lowered onto the sample carrier before said spraying phase, and raised again after said passive settling phase and removed from the sample carrier.

13. The method according to claim 9, wherein
    after the passive settling phase the remaining mist is removed from said container.

14. The method according to claim 9, wherein in an additional cleaning phase a neutral or cleaning liquid is sprayed through the spray head for cleaning said container.

15. The method according to claim 9 wherein
    a homogeneous distribution of said droplets 4 in said container is achieved by a suitable choice of said movement of said spray head and of the distance between the spray head and the sample carrier during the spraying.

16. The method according to claim 9, wherein
    local deviations of the amount of reagent solution applied to said sample carrier are smaller than 5%.

17. The method according to claim 9, wherein
    an end-of-spray time marking the end of the spraying phase is determined visually or based on a change in the energy demand of the spray head.

18. Derivatization apparatus for coating a sample carrier prior to the analysis of the sample comprising:
    a reservoir for a reagent solution;
    a spray nozzle with a spray head and a container in which at least a part of the sample carrier is located, wherein said container is hermetically sealed;
    wherein said spray head is located at a bottom of said container and said spray head is disposed adjacent to said sample carrier;
    and wherein said reagent solution is configured to be sprayed upwardly into said container by said spray head in order to generate in said container a homogeneous mist of droplets of said reagent solution.

19. Derivatization apparatus for coating a sample carrier prior to the analysis of the sample of claim 18 wherein:
an opening is formed through a bottom of said container to allow insertion of the sample carrier, said opening is configured to be hermetically sealed.

* * * * *